United States Patent
Ootsuka et al.

(10) Patent No.: US 9,765,004 B2
(45) Date of Patent: *Sep. 19, 2017

(54) α,α-DIFLUOROACETALDEHYDE PRODUCTION METHOD (71) Applicant: Central Glass Company, Limited, Ube-shi, Yamaguchi (JP)

(72) Inventors: Takashi Ootsuka, Kawagoe (JP); Mari Imamura, Kawagoe (JP); Akihiro Ishii, Kawagoe (JP); Koji Ueda, Kawagoe (JP); Shunsuke Mimura, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/227,628

(22) Filed: Aug. 3, 2016

(65) Prior Publication Data

US 2016/0340284 A1 Nov. 24, 2016

Related U.S. Application Data (63) Continuation of application No. 14/761,774, filed as application No. PCT/JP2014/051365 on Jan. 23, 2014, now Pat. No. 9,440,900.

(30) Foreign Application Priority Data

Jan. 25, 2013 (JP) ................................ 2013-012532

(51) Int. Cl.
C07C 45/41 (2006.01)

(52) U.S. Cl.
CPC ............ *C07C 45/41* (2013.01); *Y02P 20/582* (2015.11)

(58) Field of Classification Search
CPC .................................................... C07C 45/41
USPC ........................................................ 568/484
See application file for complete search history.

(56) References Cited

U.S. PATENT DOCUMENTS

| | | |
|---|---|---|
| 6,180,830 B1 | 1/2001 | Jacquot |
| 8,471,048 B2 | 6/2013 | Kuriyama et al. |
| 8,658,840 B2 | 2/2014 | Ishii et al. |
| 9,024,075 B2 | 5/2015 | Ishii et al. |
| 2011/0237814 A1 | 9/2011 | Kuriyama et al. |
| 2013/0303774 A1 | 11/2013 | Ishii et al. |
| 2014/0194654 A1 | 7/2014 | Ishii et al. |

FOREIGN PATENT DOCUMENTS

| | | |
|---|---|---|
| JP | 11-501575 A | 2/1999 |
| WO | WO 2011/048727 A1 | 4/2011 |
| WO | WO 2012/105431 A1 | 8/2012 |
| WO | WO 2013/018573 A1 | 2/2013 |

OTHER PUBLICATIONS

International Search Report (PCT/ISA/210) dated Mar. 11, 2014, with English translation (Four (4) pages).
Kaneko, et al. "A Remarkably Simple Route to Versatile Difluoromethylated Molecules", J. Org. Chem. 1993, 58, pp. 2302-2312, (Eleven (11) pages).
Daijiten, et al., 1989, Tokyo Kagaku Dojin, pp. 596-597, with partial English translation (Four (4) pages).
Greene, et al. "Protective Groups in Organic Synthesis", Third Edition, 1999, John Wiley & Sons, Inc., 1999, (Twenty Eight (28) pages).
Hegedus, "Transition Metals in the Synthesis of Complex Organic Molecules", Second Edition, pp. 4-9, Tokyo Kagaku Dojin, 2001, with partial English translation (Eight (8) pages).
Noyori et al. "Organic Chemistry for Graduate Students vol. II: Molecular Structure & Reaction/Organic Metal Chemistry", Tokyo Kagaku Dojin, 1999, pp. pp. 388-391, with partial English translation (Five (5) pages).
Spasyuk, et al. "Replacing Phosphorus with Sulfur for the Efficient Hydrogenation of Esters", Agnew. Chem. Int. Ed. 2013, 52, pp. 2538-2542, (Five (5) pages).
Spasyuk, et al. "Acceptorless Dehydrogenative Coupling of Ethanol and Hydrogenation of Esters and Imines", Organometallics, 2012, 31, pp. 5239-5242, (Four (4) pages).
Spasyuk, et al. "From Esters to Alcohols and Back with Ruthenium and Osmium Catalysts", Agnew. Chem. Int. Ed. 2012, 51, pp. 2772-2775, (Four (4) pages).
Zhang, et al. "Efficient Homogeneous Catalytic Hydrogenation of Esters to Alcohols", Agnew. Chem. Int. Ed. 2006, 45, pp. 1113-1115, (Three (3) pages).
Ishii, et al. "Trifluoroacetaldehyde", Journal of Synthetic Organic Chemistry, Japan, 1999, vol. 57, No. 10, pp. 102-104, with partial English translation (Four (4) pages).
Dub, et al. "Catalytic Reductive Transformations of Carboxylic and Carbonic Acid Derivatives Using Molecular Hydrogen", ACS Catalysis, 2012, vol. 2, pp. 1718-1741, (Twenty Four (24) pages).
Otsuka, et al. "Practical Selective Hydrogenation of α-Fluorinated Esters with Bifunctional Pincer-Type Rutehnium(II) Catalysts Leading to Fluorinated Alcohols or Fluoral Hemiacetals", Journal of the American Chemical Society, 2013, vol. 135, pp. 9600-9603, Four (4) pages).

*Primary Examiner* — Sikarl Witherspoon
(74) *Attorney, Agent, or Firm* — Crowell & Moring LLP (57) ABSTRACT

A production method of α,α-difluoroacetaldehyde according to the present invention includes reaction of an α,α-difluoroacetic acid ester with hydrogen gas ($H_2$) in the presence of a ruthenium catalyst. It is possible to selectively obtain α,α-difluoroacetaldehyde as a partially reduced product of the hydrogenation reaction by the adoption of specific reaction conditions (in particular, reaction solvent and reaction temperature). This hydrogenation process can be alternative to the industrially unpractical hydride reduction process.

16 Claims, No Drawings

α,α-DIFLUOROACETALDEHYDE PRODUCTION METHOD

CROSS REFERENCE TO RELATED APPLICATIONS

This application is a continuation of U.S. application Ser. No. 14/761,774, filed Jul. 17, 2015, which is a 371 of International Application No. PCT/JP2014/051365, filed Jan. 23, 2014, which claims priority from Japanese Patent Application No. 2013-012532, filed Jan. 25, 2013, the disclosures of which are expressly incorporated by reference herein.

FIELD OF THE INVENTION

The present invention relates to a method for industrial production of an α,α-difluoroacetaldehyde.

BACKGROUND ART

There is known a process for producing α,α-difluoroacetaldehyde by partial reduction of an α,α-difluoroacetic acid ester. However, this partial reduction process is limited to the use of a stoichiometric amount of hydride reduction agent such as lithium aluminum hydride (see Non-Patent Document 1).

It is herein noted that the present applicant has filed patent applications (see Patent Documents 1 and 2) technically relevant to the present invention.

PRIOR ART DOCUMENTS

Patent Documents

Patent Document 1: International Publication No. WO 2012/105431
Patent Document 2: International Publication No. WO 2013/018573

Non-Patent Documents

Non-Patent Document 1: J. Org. Chem. (U.S.), 1993, vol. 58, p. 2302-2312

SUMMARY OF THE INVENTION

Problems to be Solved by the Invention

The above-described conventional production process, which uses the stoichiometric amount of hydride reduction agent, is not suitable for large-scale production of α,α-difluoroacetaldehyde due to the facts that: the hydride reduction agent is expensive and needs to be handled with great caution; and the post-treatment of the resulting reaction product requires a complicated operation and causes a large amount of waste. Further, the above-described conventional production process requires extremely-low-temperature conditions to suppress the generation of β,β-difluoroethanol as a by-product so that it is industrially difficult to implement this conventional production process.

It is accordingly an object of the present invention to provide a method for industrial production of α,α-difluoroacetaldehyde. More specifically, it is an object of the present invention to find out a highly practical process for partial reduction of an α,α-difluoroacetic acid ester as an alternative to the above hydride reduction process. As far as the present inventors know, there has been made no report about the production of α,α-difluoroacetaldehyde by reaction of an α,α-difluoroacetic acid ester with hydrogen gas ($H_2$) in the presence of a ruthenium catalyst, notably a homogeneous catalyst, as disclosed in the present invention. In the present specification, the term "homogeneous catalyst" refers a catalyst defined in Kagaku Daijiten (Tokyo Kagaku Dojin, edited by Michinori Ohki, Toshiaki Osawa, Motoharu Tanaka and Hideaki Chihara) and the like.

Means for Solving the Problems

As a result of extensive researches made in view of the above circumstances, the present inventors have found that a ruthenium catalyst, preferably a homogeneous ruthenium catalyst, more preferably a ruthenium complex of the following general formula [2], still more preferably a ruthenium complex of the following general formula [4], can be used as an effective catalyst or precursor thereof for partial reduction of an α,α-difluoroacetic acid ester.

[2]

In the general formula [2], R each independently represents a hydrogen atom, an alkyl group, a substituted alkyl group, an aromatic ring group or a substituted aromatic ring group; Ar each independently represents an aromatic ring group or a substituted aromatic ring group; X each independently represents a ligand with a formal charge of −1 or 0 (with the proviso that the sum of the formal charges of three X is −2); and n each independently represents an integer of 1 or 2.

[4]

In the general formula [4], Ph each independently represent a phenyl group.

Each of the ruthenium complexes of the general formulas (2) and (4) functions as a homogeneous ruthenium catalyst.

The present applicant has filed two patent applications (Patent Documents 1 and 2) technically relevant to the present invention as mentioned above.

The present invention is clearly different from Patent Document 1 in that, although the raw substrate of the present invention falls within the range of α-fluoroester as the raw substrate of Patent Document 1, the target product of the present invention is α,α-difluoroacetaldehyde; and the target product of Patent Document 1 is β-fluoroalcohol. The present inventors have found that, even with the use of the same ruthenium complex, it is possible to selectively obtain α,α-difluoroacetaldehyde as a partially reduced product of the hydrogenation reaction by the adoption of specific reaction conditions (in particular, reaction solvent and reaction temperature) as disclosed in the present invention. In the present invention, β,β-difluoroethanol (as one kind of β-fluoroalcohol) is generated as a by-product. There is thus no limitation imposed by the present invention on Patent Document 1. Further, the by-produced β,β-difluoroethanol can be easily separated by purification from the target α,α-difluoroacetaldehyde in the present invention because of the large difference between the physical properties of the α,α-difluoroacetaldehyde (including the after-mentioned equivalent form) and the β,β-difluoroethanol. There is thus no limitation imposed by Patent Document 1 on the production method of the α,α-difluoroacetaldehyde according to the present invention.

On the other hand, the present invention is clearly different from Patent Document 2 in the raw substrate. The raw substrate of the present invention corresponds to that, in the α-fluoroester as the raw substrate of Patent Document 2, $R^1$ is a hydrogen atom (vs. a halogen atom or haloalkyl group).

In this way, the present inventors have found novel techniques for production of α,α-difluoroacetaldehyde by a hydrogenation process other than the hydride reduction process. The present invention is based on such findings.

The present invention thus provides methods for production of α,α-difluoroacetaldehyde as defined by the following aspects 1 to 12.

Inventive Aspect 1

A method for producing α,α-difluoroacetaldehyde of the formula [3], comprising: reaction of an α,α-difluoroacetic acid ester of the general formula [1] with hydrogen gas ($H_2$) in the presence of a ruthenium complex of the general formula [2],

[1]

where $R^1$ represents an alkyl group or a substituted alkyl group,

[2]

where R each independently represents a hydrogen atom, an alkyl group, a substituted alkyl group, an aromatic ring group or a substituted aromatic ring group; Ar each independently represents an aromatic ring group or a substituted aromatic ring group; X each independently represents a ligand with a formal charge of −1 or 0 (with the proviso that the sum of the formal charges of three X is −2); and n each independently represents an integer of 1 or 2,

[3]

Inventive Aspect 2

The method according to Inventive Aspect 1, wherein the reaction is performed in the presence of a base.

Inventive Aspect 3

A method for producing α,α-difluoroacetaldehyde of the formula [3], comprising: reaction of an α,α-difluoroacetic acid ester of the general formula [1] with hydrogen gas ($H_2$) in the presence of a ruthenium complex of the general formula [4] and a base,

[1]

where $R^1$ an alkyl group or a substituted alkyl group,

[4]

where Ph represents a phenyl group,

[3]

Inventive Aspect 4

The method according to any one of Inventive Aspects 1 to 3, wherein the α,α-difluoroacetic acid ester of the general formula [1] is an α,α-difluoroacetic acid ester of the general formula [5],

[5]

where $R^2$ is an alkyl group.

Inventive Aspect 5

The method according to any one of Inventive Aspects 1 to 4, wherein the reaction is performed at a reaction temperature of 30° C. or lower with the use of an alcohol solvent as a reaction solvent.

Inventive Aspect 6

The method according to any one of Inventive Aspects 1 to 4, wherein the reaction is performed at a reaction temperature of 20° C. or lower with the use of an alcohol solvent as a reaction solvent.

Inventive Aspect 7

The method according to any one of Inventive Aspects 1 to 4, wherein the reaction is performed at a reaction temperature of 50° C. or lower with the use of an aliphatic hydrocarbon solvent, an aromatic hydrocarbon solvent, a halogenated solvent or an ether solvent as a reaction solvent.

Inventive Aspect 8

The method according to any one of Inventive Aspects 1 to 4, wherein the reaction is performed at a reaction temperature of 40° C. or lower with the use of an aliphatic hydrocarbon solvent, an aromatic hydrocarbon solvent, a halogenated solvent or an ether solvent as a reaction solvent.

Inventive Aspect 9

A method for producing α,α-difluoroacetaldehyde of the formula [3], comprising: reaction of an α,α-difluoroacetic acid ester of the general formula [1] with hydrogen gas ($H_2$) in the presence of a ruthenium catalyst,

[1]

where $R^1$ represents an alkyl group or a substituted alkyl group,

[3]

Inventive Aspect 10

The method according to Inventive Aspect 9, wherein the ruthenium catalyst is a homogeneous catalyst.

Inventive Aspect 11

The method according to any one of Inventive Aspects 1 to 10, comprising:

stopping the reaction at the time when the selectivity of the α,α-difluoroacetaldehyde of the formula [3] and β,β-difluoroethanol is α,α-difluoroacetaldehyde:β,β-difluoroethanol=90 or more:10 or less; and recovering and recycling unreacted α,α-difluoroacetic acid ester.

Inventive Aspect 12

The method according to any one of Inventive Aspects 1 to 11, further comprising post-treatment to, when the α,α-difluoroacetaldehyde is obtained as a stable equivalent of the general formula [6] or [7], purify the α,α-difluoroacetaldehyde as a hemiacetal of the general formula [8] by contact of the stable equivalent with methanol or ethanol,

[6]

where $R^3$ represents a methyl group or an ethyl group,

[7]

where $R^4$ represents a methyl group or an ethyl group,

[8]

The production method of the present invention utilizes the hydrogenation process alternative to the industrially unpractical hydride reduction process. The production method of the present invention is highly practical in that: the hydrogenation process does not require high-pressure facility and can be performed with a high substrate/catalyst ratio; and the target product can be mainly readily obtained only by distillation in the post-treatment process. Thus, the production method of the present invention provides solutions to all problems in the background art and enables industrial production of the α,α-difluoroacetaldehyde.

DETAILED DESCRIPTION OF THE INVENTION

The production method of the α,α-difluoroacetaldehyde according to the present invention will be described below in detail. It should be understood that: the scope of the present invention is not limited to the following examples; and various changes and modifications can be made as appropriate without impairing the scope of the present invention. All of the publications cited in the present specification, such as prior art documents and patent documents e.g. published patents and patent applications, are herein incorporated by reference. In the following description, the structures of the general formulas [1] to [8] are as defined above.

In the present invention, the α,α-difluoroacetaldehyde of the formula [3] is produced by reaction of the α,α-difluoroacetic acid ester of the general formula [1] with hydrogen gas ($H_2$) in the presence of the ruthenium complex of the general formula [2].

In the α,α-difluoroacetic acid ester of the general formula [1], $R^1$ represents an alkyl group or a substituted alkyl group. Examples of the alkyl group are those of 1 to 18 carbon atoms having a straight-chain structure, a branched structure or a cyclic structure (in the case of 3 or more carbon atoms). Examples of the substituted alkyl group are those obtained by substitution of any number of and any combination of substituents on any of carbon atoms of the above alkyl groups. As such substituents, there can be used: halogen atoms such as fluorine, chlorine and bromine; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; cyano group; lower alkoxycarbonyl groups such as methoxycarbonyl, ethoxycarbonyll and propoxycarbonyl; aromatic-ring groups such as phenyl, naphthyl, anthryl, pyrrolyl (including nitrogen-protected form), pyridyl, furyl, thienyl, indolyl (including nitrogen-protected form), quinolyl, benzofuryl and benzothienyl; carboxyl group; protected carboxyl groups; amino group; protected amino groups; hydroxyl group; and protected hydroxyl groups. In the substituted alkyl group, an arbitrary carbon-carbon single bond or bonds may be replaced by any number of and any combination of carbon-carbon double bonds and carbon-carbon triple bonds. (As a matter of course, the alkyl group with such an unsaturated bond or bonds may have any of the above substituent groups.) Depending on the kind of the substituent group, the substituent group itself may be involved in a side reaction. However, the side reaction can be minimized by the adoption of suitable reaction conditions.

In the present specification, the term "lower" means that the group to which the term is attached is a group of 1 to 6 carbon atoms having a straight-chain structure, a branched structure or a cyclic structure (in the case of 3 or more carbon atoms). The aromatic ring groups described above as "such substituent groups" may further be substituted with a halogen atom, a lower alkyl group, a lower haloalkyl group, a lower alkoxy group, a lower haloalkoxy group, a cyano group, a lower alkoxycarbonyl group, a carboxyl group, a protected carboxyl group, an amino group, a protected amino group, a hydroxyl group, a protected hydroxyl group etc. As the protecting groups of the pyrrolyl, indolyl, carboxyl, amino and hydroxyl groups, there can be used those described in "Protective Groups in Organic Synthesis", Third Edition, 1999, John Wiley & Sons, Inc.

Herein, it is in the scope of the present invention that the substrate compound actually subjected to hydrogenation reaction falls within the range of the α,α-difluoroacetic acid ester of the general formula [1]. For example, it is conceivable that α,α-difluorophenylacetic acid ester is used as the raw substrate and converted to a corresponding methyl ester by ester interchange such that the methyl ester would be subjected to hydrogenation reaction. Such a case is included in the scope of the present invention.

Among the α,α-difluoroacetic acid ester of the general formula [1], the α,α-difluoroacetic acid ester of the general formula [5] is preferred because it is easily available on a large scale. As a matter of course, the alkyl group as $R^2$ in the α,α-difluoroacetic acid ester of the general formula [5] is the same as the alkyl group as $R^1$ in the α,α-difluoroacetic acid ester of the general formula [1].

In the ruthenium complex of the general formula [2], R each independently represent a hydrogen atom, an alkyl group, a substituted alkyl group, an aromatic ring group or a substituted aromatic ring group. Examples of the alkyl and substituted alkyl groups as R are the same as those of $R^1$ in the α,α-difluoroacetic acid ester of the general formula [1]. Examples of the aromatic ring group are those of 1 to 18 carbon atoms, such as: aromatic hydrocarbon groups as typified by phenyl, naphthyl and anthryl; and aromatic heterocyclic groups containing heteroatoms e.g. as nitrogen, oxygen or sulfur as typified by pyrrolyl (including nitrogen-protected form), pyridyl, furyl, thienyl, indolyl (including nitrogen-protected form), quinolyl, benzofuryl and benzothienyl. Examples of the substituted aromatic ring group are those obtained by substitution of any number of and any combination of substituents on any of carbon or nitrogen atoms of the above aromatic ring groups. As such substituents, there can be used the same substituents as mentioned above. Two vicinal R (except hydrogen atoms) may form a cyclic structure by covalent bond of carbon atoms with or without a nitrogen atom, an oxygen atom or a sulfur atom. It is particularly preferable that all of eight R are hydrogen (in the case where each of two n is 1).

In the ruthenium complex of the general formula [2], Ar each independently represent an aromatic ring group or a substituted aromatic ring group. Examples of the aromatic ring and substituted aromatic ring groups as Ar are the same as those of R in the ruthenium complex of the general formula [2]. It is particularly preferable that all of four Ar are phenyl.

In the ruthenium complex of the general formula [2], X each independently represent a ligand having a formal charge of −1 or 0 with the proviso that the sum of the formal charges of three X is −2 (the formal charge of Ru is +2). Examples of the ligand having a formal charge of −1 or 0 are: ligands described in Hegedus: "Transition Metals in the Synthesis of Complex Organic Molecules" (written by L. S. Hegedus, Second Edition, translated by Shinji Murai, p. 4-9, Tokyo Kagaku Dojin, 2001) and in Organic Chemistry for Graduate Students Vol. II: "Molecular Structure & Reaction/Organic Metal Chemistry" (Ryoji Noyori et al., p. 389-390, Tokyo Kagaku Dojin, 1999) etc.; $BH_4^-$; and $R^5CO_2^-$. (Herein, $R^5$ represents a hydrogen atom, an alkyl group or a substituted alkyl group. Examples of the alkyl and substituted alkyl groups as $R^5$ are the same as those of $R^1$ in the α,α-difluoroacetic acid ester of the general formula [1].) It is particularly preferable that the three ligands are hydrogen, chlorine and carbon monoxide, respectively.

The reaction can be performed in the presence of no base in the case where at least one of three X ligands is $BH_4$ in the ruthenium complex of the general formula [2]. (As a matter of course, it is alternatively feasible to perform the reaction in the presence of the base). Among others, it is preferable to use the ruthenium complex of the general formula [4] in which the Cl ligand has been replaced by $BH_4(H\text{—}BH_3)$ (see International Application Publication No. 2011/048727).

Further, n each independently represent an integer of 1 or 2 in the ruthenium complex of the general formula [2]. In the case where n is 1, a nitrogen atom and a phosphorus atom are bonded to each other via two carbon atoms in the ruthenium complex. In the case where n is 2, a nitrogen atom and a phosphorus atom are bonded to each other via three carbon atoms in the ruthenium complex. It is preferable that each of two n is 2.

In the ruthenium complex of the general formula [4], Ph represents a phenyl group.

Among the ruthenium complex of the general formula [2], the ruthenium complex of the general formula [4] is preferred. There can be used, as the ruthenium complex of the general formula [4], a commercially available complex Ru-MACHO™ (manufactured by Takasago International Corporation). The ruthenium complex of the general formula [2] can be prepared in a similar manner with reference to the preparation process of the complex Ru-MACHO™. Further, the ruthenium complex of the general formula [2] can be used even when water or organic solvent such as toluene is contained in the ruthenium complex. It suffices that the purity of the ruthenium complex is 70% or higher. The purity of the ruthenium complex is preferably 80% or higher, more preferably 90% or higher.

It suffices to use the ruthenium complex of the general formula [2] in an amount of 0.000001 mol or more per 1 mol of the α,α-difluoroacetic acid ester of the general formula [1]. The amount of the ruthenium complex of the general formula [2] is preferably 0.00001 to 0.005 mol, more preferably 0.00002 to 0.002 mol, per 1 mol of the α,α-difluoroacetic acid ester of the general formula [1].

Examples of the base usable in the reaction are: alkali metal hydrogencarbonates such as lithium hydrogencarbonate, sodium hydrogencarbonate and potassium hydrogencarbonate; alkali metal carbonates such as lithium carbonate, sodium carbonate and potassium carbonate; alkali metal hydroxides such as lithium hydroxide, sodium hydroxide and potassium hydroxide; tetraalkyl ammonium hydroxides such as tetramethyl ammonium hydroxide, tetraethyl ammonium hydroxide, tetra-n-propyl ammonium hydroxide and tetra-n-butyl ammonium hydroxide; alkali metal alkoxides such as lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide and potassium tert-butoxide; organic bases such as triethylamine, diisopropylethylamine, 4-dimethylaminopyridine and 1,8-diazabicyclo[5.4.0]undec-7-ene; alkali metal bis(trialkylsilyl)amides such as lithium bis(trialkylsilyl)amide, sodium bis(trialkylsilyl)amide and potassium bis(trialkylsilyl)amide; and alkali metal borohydrides such as lithium borohydride, sodium borohydride and potassium borohydrode. Among others, alkali metal alkoxides are preferred. Particularly preferred are lithium methoxide, sodium methoxide and potassium methoxide.

It suffices to use the base in an amount of 0.001 mol or more per 1 mol of the α,α-difluoroacetic acid ester of the general formula [1]. The amount of the base is preferably 0.005 to 5 mol, more preferably 0.01 to 3 mol, per 1 mol of the α,α-difluoroacetic acid ester of the general formula [1].

As it is assumed that the true catalytic active species is derived from the ruthenium catalyst of the general formula [2] optionally in the presence of the base, the case where the catalytic active species (including isolated form) is prepared in advance and used in the hydrogenation reaction is covered by the scope of the present invention.

It suffices to use the hydrogen gas in an amount of 1 mol or more per 1 mol of the α,α-difluoroacetic acid ester of the general formula [1]. The hydrogen gas is preferably used in a large excessive amount, more preferably in a large excessive amount under the following pressurized conditions.

There is no particular limitation on the pressure of the hydrogen gas. The hydrogen pressure is preferably 2 to 0.001 MPa, more preferably 1 to 0.01 MPa.

Examples of the reaction solvent usable in the reaction are: aliphatic hydrocarbon solvents such as n-hexane, cyclohexane and n-heptane; aromatic hydrocarbon solvents such as toluene, xylene and mesitylene; halogenated solvents such as methylene chloride, 1,2-dichloroethane and α,α,α-trifluorotoluene; ether solvents such as diethyl ether, 1,2-dimethoxyethane, 1,4-dioxane, tetrahydrofuran, 2-methyltetrahydrofuran, tert-butyl methyl ether, diisopropyl ether, diethylene glycol dimethyl ether and anisole; alcohol solvents such as methanol, ethanol, n-propanol, isopropanol, n-butanol, tert-butanol, n-pentanol, n-hexanol and cyclohexanol; amide solvents such as N,N-dimethylformamide, N,N-dimethylacetamide and 1,3-dimethyl-2-imidazolidinone; nitrile solvents such as acetonitrile, propionitrile and benzonitrile; dimethyl sulfoxide; and water. Among others, aliphatic hydrocarbon solvents, aromatic hydrocarbon solvents, halogenated solvents, ether solvents and alcohol solvents are preferred. Particularly preferred are aliphatic hydrocarbon solvents, aromatic hydrocarbon solvents, ether solvents and alcohol solvents. These reaction solvents can be used solely or in combination of two or more thereof. The reaction solvent as specified in the following claims 5 to 8 (alcohol solvent, aliphatic hydrocarbon solvent, aromatic hydrocarbon solvent, halogenated solvent and ether solvent) can be in the form of a mixture of two or more kinds of reaction solvents with the proviso that the volume ratio of the specified reaction solvent is the highest. For instance, a mixed solvent of methanol and tert-butyl methyl ether was used in the after-mentioned Examples 11 and 12. In Example 11, the volume ratio of the tert-butyl methyl ether was higher so that the mixed solvent was specified as an ether reaction solvent. In Example 12, the volume ratio of the methanol was higher so that the mixed solvent was specified as an alcohol reaction solvent. The alcohol reaction solvent (hereinafter referred to as "solvent A") has the effect of increasing the rate of the reaction, whereas the aliphatic hydrocarbon, aromatic hydrocarbon, halogenated or ether reaction solvent (hereinafter referred to as "solvent B") has the effect of suppressing the generation of β,β-difluoroethanol due to over-reduction. It is a preferred embodiment to use a mixed solvent of these solvents A and B (as Embodiment 1; see the after-mentioned Examples 11-13) in order to maximize the usability of the present invention. It suffices that the volume ratio (A:B) of the solvents A and B is 60 or more:40 or less (assuming the total volume of the solvents A and B as 100). The volume ratio of the solvents A and B is preferably 70 or more:30 or less, more preferably 80 or more:20 or less. As a matter of course, the solvent B can be used alone or in combination of the solvent A as a minor component.

It suffices to use the reaction solvent in an amount of 0.03 L (liter) or more per 1 mol of the α,α-difluoroacetic acid ester of the general formula [1]. The amount of the reaction solvent is preferably 0.05 to 10 L, more preferably 0.07 to 7 L, per 1 mol of the α,α-difluoroacetic acid ester of the general formula [1].

It suffices that the reaction temperature is +30° C. or lower in the case where the alcohol solvent is used as the reaction solvent. In this case, the reaction temperature is preferably +25 to −50° C., more preferably +20 to −40° C., still more preferably +15 to −30° C. It suffices that the reaction temperature is +50° C. or lower in the case where the aliphatic hydrocarbon solvent, aromatic hydrocarbon solvent, halogenated solvent or ether solvent is used as the reaction solvent. In this case, the reaction temperature is preferably +45 to −30° C., more preferably +40 to −20° C., still more preferably +35 to −10° C.

In order to make the best use of the advantages of the present invention, it is preferable to perform the reaction under the conditions of a reaction temperature of 20° C. or lower with the use of the alcohol solvent as the reaction solvent or a reaction temperature of 40° C. or lower with the use of the aliphatic hydrocarbon solvent, aromatic hydrocarbon solvent, halogenated solvent or ether solvent as the reaction solvent Further, it suffices that the reaction time is 72 hours or less. As the reaction time varies depending on the raw substrate and reaction conditions, it is preferable to determine the time at which there is seen almost no decrease of the raw substrate as the end of the reaction while monitoring the progress of the reaction by any analytical means such as gas chromatography, liquid chromatography or nuclear magnetic resonance.

In the present invention, the hydrogenation catalyst or precursor thereof is not limited to the ruthenium complex of the general formula [2] or [4]. There can alternatively be used an existing ruthenium catalyst as the hydrogenation catalyst or precursor thereof in the present invention. Examples of such an existing ruthenium catalyst are those described in: Angew. Chem. Int. Ed., 2013, 52, 2538-2542; Organometallics, 2012, 31, 5239-5242; Angew. Chem. Int. Ed., 2012, 51, 2772-2775; and Angew. Chem. Int. Ed., 2006, 45, 1113-1115, as typified below (as homogeneous ruthenium catalysts) in FIG. 1. These ruthenium catalysts can be used under the same reaction conditions (such as the amount of the catalyst used, the kind and amount of the base optionally used, the amount of the hydrogen gas used, the hydrogen pressure, the kind and amount of the reaction solvent used, the reaction temperature, the reaction time, the post-treatment process and preferred embodiments) as the ruthenium complex of the general formula [2] or [4].

FIG. 1

The α,α-difluoroacetaldehyde of the general formula [3] can be obtained by any ordinary organic synthesis post-treatment process. As the α,α-difluoroacetaldehyde of the general formula [3] is an aldehyde having directly bonded thereto a strong electron-attracting difluoromethyl group, it is often the case that the α,α-difluoroacetaldehyde of the general formula [3] is formed as a stable equivalent such as a self-polymerization product, hydrate, hemiacetal, acetal or combination of structural features thereof. (As a matter of course, the α,α-difluoroacetaldehyde of the general formula [3] can be obtained in the form of an aldehyde.) In the scope of the present invention, this stable equivalent falls within the range of the α,α-difluoroacetaldehyde of the general formula [3]. It is herein noted that the alcohol function of the hemiacetal or acetal is derived from the alkali metal alkoxide used as the base, the alcohol used as the reaction solvent, the ester moiety of the raw substrate (i.e. $OR^1$ in the α,α-difluoroacetic acid ester of the general formula [1]), β,β-difluoroethanol generated as a by-product due to over-reduction or the like.

Typical examples of the stable equivalent of the α,α-difluoroacetaldehyde of the general formula [3] are those shown below in FIG. 2 (where the abbreviations Me and Et refer to methyl and ethyl, respectively). The stable equivalent is not however limited to these typical examples.

FIG. 2

Figure 2:
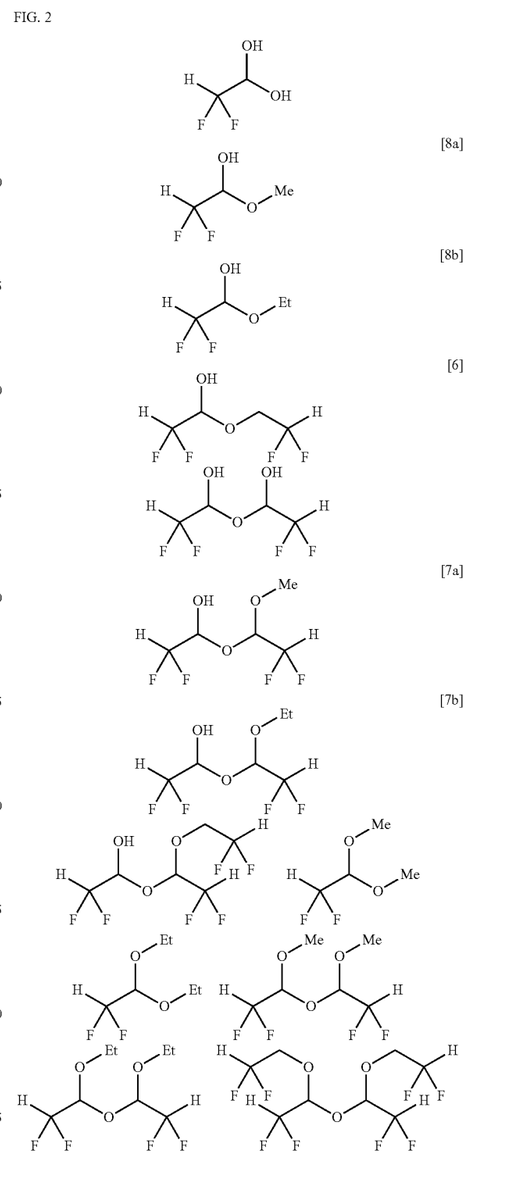

The present inventors have found, as a post-treatment process, purification operation to, when the α,α-difluoroacetaldehyde includes a stable equivalent, particularly of the general formula [6] or [7] ([7a], [7b]) as shown in FIG. 2, convert the stable equivalent to a hemiacetal of the general formula [8] by contact with methanol or ethanol. This purification operation is simple and industrially practical. Among various stable equivalents, the hemiacetal of the general formula [8] ([8a], [8b]) is a compound having good reactivity as an organic synthesis intermediate for various reactions and easy to handle in industrial production applications. On the other hand, the stable equivalent of the general formula [6] is a hemiacetal derived from the over-reduced β,β-difluoroethanol by-product. The stable equivalent of the general formula [7] ([7a], [7b]) is a dimer formed by addition of the hemiacetal of the general formula [8] to the α,α-difluoroacetaldehyde when isolated due to reverse reaction. The stable equivalent of the general formula [6], [7] is generated in the case where the amount of coexistence of methanol or ethanol relative to the hemiacetal of the general formula [8] (e.g. at the time of recovery of the main distillate fraction during fractional distillation). In order to obtain the useful hemiacetal compound (intermediate) of the general formula [8] with high purity (in particular, 90 mol % or higher), it is important to carry out purification operation to convert (derive) the coexisting minor component, that is, stable equivalent of the general formula [6], [7] to the hemiacetal of the general formula [8]. The purification operation needs to be simple for industrial production applications. It is herein noted that, during post-treatment in the production of similar fluoral (α,α,α-trifluoroacetaldehyde), there is generated almost no compound corresponding to the stable equivalent of the general formula [6], [7] (by substitution of a trifluoromethyl group with a difluoromethyl group). The generation of such a stable equivalent is a specific problem to be solved in the present invention (the production method of the α,α-difluoroacetaldehyde).

In the stable α,α-difluoroacetaldehyde equivalent of the general formula [7], $R^3$ represents a methyl group or an ethyl group. In the α,α-difluoroacetaldehyde hemiacetal of the general formula [8], $R^4$ represents a methyl group or an ethyl group. There is no particular limitation on the technique of contact of the stable equivalent with the methanol or ethanol. The stable equivalent can be brought into contact with the methanol or ethanol by any ordinary organic synthesis operation. It suffices to use the methanol or ethanol in an amount of 0.7 mol or more per 1 mol of the total amount of the stable α,α-difluoroacetaldehyde equivalent [6], [7]. The amount of the methanol or ethanol used is preferably 0.8 to 500 mol, more preferably 0.9 to 300 mol, per 1 mol of the total amount of the stable α,α-difluoroacetaldehyde equivalent [6], [7]. It suffices that the contact temperature is −20° C. or higher. The contact temperature is preferably 0 to +150° C., more preferably +20 to +125° C. It suffices that the contact time is 48 hours or less.

As the contact time varies depending on the stable equivalent (general formula [6] or [7]) and contact conditions, it is preferable to determine the time at which there is seen almost no decrease of the stable equivalent as the end of the contact while monitoring the progress of the contact by any analytical means such as gas chromatography, liquid chromatography or nuclear magnetic resonance. It is optionally feasible to carry out the contact in the presence of an acid for smooth conversion of the stable equivalent to the hemiacetal (general formula [8]). As such an acid, there can be the same kind of acid as those mentioned later as an "acid for neutralization of the reaction completed solution". Even in the absence of the acid, the contact proceeds favorably by the adoption of suitable contact conditions. In the case where the contact is carried out with the use of water in place of the methanol or ethanol, the stable equivalent can be obtained as a hydrate with high yield.

The crude product (α,α-difluoroacetaldehyde or its stable equivalent) can be purified to a high degree, as needed, by activated carbon treatment, fractional distillation, recrystallization, column chromatography or the like. It is convenient to recover the target product by directly subjecting the reaction completed solution to recovery distillation in the case where the target product has a low boiling point. In the case where the reaction is performed in the presence of the base, the relatively highly acidic target product (self-polymerization product, hydrate, hemicacetal etc.) tends to form a salt or complex with the base and remain in the residue of recovery distillation. Further, the target product may undergo Cannizzaro reaction in the presence of the base. In these cases, it is feasible to obtain the target product with high yield by neutralizing the reaction completed solution with an organic acid such as formic acid, acetic acid, citric acid, oxalic acid, benzoic acid, methanesulfonic acid or paratoluenesulfonic acid or an inorganic acid such as hydrogen chloride, hydrogen bromide, nitric acid or sulfuric acid in advance, and then, subjecting the neutralized reaction completed solution to recovery distillation (including recovery by washing the distillation residue with an organic solvent such as tert-butyl methyl ether, diisopropyl ether, methanol or ethanol and, optionally, filtration of the generated salt).

In some cases, it is possible to easily obtain the target product with high purity by fractional distillation of the crude product (i.e., target product obtained by recovery distillation) in the case where the reaction is performed with higher priority given to the conversion rate than to the selectivity. Such a reaction technique is a preferred embodiment (as Embodiment 2). In the reaction of the present invention, the selectivity decreases with increase in the conversion rate. The target product can be obtained with high selectivity (e.g. target product: β,β-difluoroethanol=90 or more:10 or less as will be explained below) by stopping the reaction at the time when the conversion rate is 65% or lower. The selectivity (target product: β,β-difluoroethanol assuming their total amount as 100) can be 60 or more:40 or less and is preferably 70 or more:30 or less, more preferably 80 or more:20 or less, still more preferably 90 or more:10 or less. In particular, there is no need to perform high-theoretical-plate-number fractional distillation for purification of the target product when the selectivity is 90 or more:10 or less (for example, the product can be commercialized from the recovered distillation residue; see Examples 20 and 21).

It is possible in some cases to easily obtain the target product with high purity by fractional distillation after converting to a hemiacetal whose boiling point is largely different from that of the by-produced β,β-difluoroethanol. Such a purification technique is also a preferred embodiment (as Embodiment 3). In this case, the alcohol function of the hemiacetal can be ethanol, n-propanol, isopropanol or n-butanol. Among others, ethanol, n-propanol or n-butanol is preferred. Particularly preferred is ethanol or n-propanol. The target product can be obtained with high purity by high-theoretical-plate-number fractional distillation even when converted to a methanol hemiacetal.

Further, it is a preferred embodiment to recover unreacted raw substrate (α,α-difluoroacetic acid ester) by fractional distillation and recycle the recovered raw substrate (as Embodiment 4). In this case, the fractional distillation can be carried out under slightly reduced pressure at which the distillation temperature becomes 70° C. or lower or under atmospheric pressure. It is particularly preferable (as Embodiment 5) to recover and recycle the unreacted raw substrate and to perform the reaction with higher priority given to the selectivity than to the conversion rate (Embodiment 2). (See Examples 20 and 21 for Embodiments 2 to 5.)

It is feasible to convert the stable α,α-difluoroacetaldehyde equivalent to the α,α-difluoroacetaldehyde of the general formula [3] as in the case of a stable equivalent of similar fluoral (as described in e.g. Journal of Synthetic Organic Chemistry, Japan, 1999, vol. 57, no. 10, p. 102-104) (see Examples 22 and 23).

EXAMPLES

The present invention will be described in more detail below by way of the following examples. It should be understood that the following examples are illustrative and are not intended to limit the present invention thereto. In the following description, the abbreviations Me, Ph, Et and t-Bu refer to methyl, phenyl, ethyl and tert-butyl, respectively.

Comparative Examples 1-4 and Examples 1-13

In Comparative Examples 1-4 and Examples 1-13, production experiments were carried out by the following general production process. The production experiment results are summarized in TABLE 1.

General Production Production

A pressure-proof reaction vessel of stainless steel (SUS) was charged with a predetermined amount (1 eq) of α,α-difluoroacetic acid ester of the following formula, a predetermined amount (purity: 94.2%; 0.0002 eq) of ruthenium complex of the following formula, a predetermined amount (0.25 eq) of base and a predetermined amount of reaction solvent.

The inside of the reaction vessel was replaced five times with hydrogen gas. The hydrogen pressure inside the reaction vessel was set to 1.0 MPa. Then, the resulting mixture inside the reaction vessel was stirred at a predetermined reaction temperature for a predetermined reaction time. The conversion rate and the selectivity of stable α,α-difluoroacetaldehyde equivalent of the following formula and over-reduced β,β-difluoroalcohol by-product of the following formula were determined by $^{19}$F-NMR analysis of the reaction completed solution.

The $^1$H- and $^{19}$F-NMR data and gas chromatographic data of the stable α,α-difluoroacetaldehyde equivalent was in agreement with those of the reference standard.

In Example 3, a methanol solution of the target product was directly recovered by distillation of the reaction completed solution. When the reaction completed solution was subjected to $^{19}$F-NMR quantification by internal standard method (internal standard material: α,α,α-trifluorotoluene), the yield of the target product was found to be approximately 60%. The target product was purified to a high degree (gas chromatographic purity: 90% or higher) by fractional distillation.

TABLE 1

| Examples | α,α-Difluoroacetic acid ester | Ruthenium complex | Base |
|---|---|---|---|
| Comparative Example 1 | 4.4 g (40 mmol) | 5.2 mg (8.0 μmol) | sodium methoxide 540 mg (10 mmol) |
| Comparative Example 2*² | 4.4 g (40 mmol) | 5.2 mg (8.0 μmol) | sodium methoxide 540 mg (10 mmol) |
| Comparative Example 3*³ | 53 g (480 mmol) | 15 mg (24 μmol) | potassium methoxide 8.4 g (120 mmol) |
| Comparative Example 4 | 4.4 g (40 mmol) | 5.2 mg (8.0 μmol) | sodium methoxide 540 mg (10 mmol) |
| Example 1 | 4.4 g (40 mmol) | 5.2 mg (8.0 μmol) | sodium methoxide 540 mg (10 mmol) |
| Example 2 | 4.4 g (40 mmol) | 5.2 mg (8.0 μmol) | sodium methoxide 540 mg (10 mmol) |
| Example 3 | 44 g (400 mmol) | 52 mg (80 μmol) | sodium methoxide 5.4 g (100 mmol) |
| Example 4 | 4.4 g (40 mmol) | 5.2 mg (8.0 μmol) | sodium methoxide 540 mg (10 mmol) |
| Example 5 | 4.4 g (40 mmol) | 5.2 mg (8.0 μmol) | sodium methoxide 540 mg (10 mmol) |

TABLE 1-continued

| Examples | | | | |
|---|---|---|---|---|
| Example 6 | 4.4 g (40 mmol) | 5.2 mg (8.0 μmol) | potassium methoxide | 700 mg (10 mmol) |
| Example 7 | 4.4 g (40 mmol) | 5.2 mg (8.0 μmol) | potassium methoxide | 700 mg (10 mmol) |
| Example 8 | 4.4 g (40 mmol) | 5.2 mg (8.0 μmol) | potassium methoxide | 700 mg (10 mmol) |
| Example 9 | 4.4 g (40 mmol) | 5.2 mg (8.0 μmol) | potassium methoxide | 700 mg (10 mmol) |
| Example 10 | 4.4 g (40 mmol) | 5.2 mg (8.0 μmol) | potassium methoxide | 700 mg (10 mmol) |
| Example 11 | 4.4 g (40 mmol) | 5.2 mg (8.0 μmol) | sodium methoxide | 540 mg (10 mmol) |
| Example 12 | 44 g (400 mmol) | 52 mg (80 μmol) | sodium methoxide | 5.4 g (100 mmol) |
| Example 13 | 4.4 g (40 mmol) | 5.2 mg (8.0 μmol) | sodium methoxide | 540 mg (10 mmol) |

| Examples | Reaction solvent | Reaction temperature | Reaction time | Conversion rate | Selectivity*[1] |
|---|---|---|---|---|---|
| Comparative Example 1 | methanol 20 ml (0.50 L/mol) | 50° C. | 6 hr. | 100% | 0:100 |
| Comparative Example 2*[2] | methanol 40 ml (1.0 L/mol) | 40° C. | all night | 100% | 0:100 |
| Comparative Example 3*[3] | methanol 240 ml (0.50 L/mol) | 40° C. | all night | 100% | 0:100 |
| Comparative Example 4 | methanol 20 ml (0.50 L/mol) | 35° C. | 6 hr. | 100% | 0:100 |
| Example 1 | methanol 20 ml (0.50 L/mol) | 30° C. | 6 hr. | 87% | 11:89 |
| Example 2 | methanol 20 ml (0.50 L/mol) | 25° C. | 6 hr. | 89% | 65:35 |
| Example 3 | methanol 200 ml (0.50 L/mol) | 20° C. | 6 hr. | 72% | 85:15 |
| Example 4 | methanol 20 ml (0.50 L/mol) | 15° C. | 6 hr. | 58% | 92:8 |
| Example 5 | methanol 20 ml (0.50 L/mol) | 5° C. | 6 hr. | 24% | 100:0 |
| Example 6 | n-hexane 20 ml (0.50 L/mol) | 40° C. | 22 hr. | 47% | 63:37 |
| Example 7 | toluene 20 ml (0.50 L/mol) | 40° C. | 22 hr. | 31% | 64:36 |
| Example 8 | 1,4-dioxane 20 ml (0.50 L/mol) | 40° C. | 18 hr. | 38% | 60:40 |
| Example 9 | tetranydrofuran 20 ml (0.50 L/mol) | 38° C. | 19 hr. | 39% | 16:84 |
| Example 10 | tert-buthyl methyl ether 20 mL (0.50 L/mol) | 40° C. | 19 hr. | 40% | 65:35 |
| Example 11 | methanol 5.7 mL + tert-buthyl methyl ether 16 mL (0.54 L/mol) | 40° C. | 10 hr. | 54% | 70:30 |
| Example 12 | methanol 197 mL + tert-buthyl methyl ether 20 mL (0.54 L/mol) | 20° C. | 6 hr. | 67% | 86:14 |
| Example 13 | methanol 3.7 mL + toluene 18 mL (0.54 L/mol) | 40° C. | 8 hr. | 65% | 59:41 |

*[1]The selectivity was determined as the ratio of α,α-difluoroacetaldehyde equivalent (target product):β,β-difluoroethanol (by-product) assuming the total amount of these product compounds as 100.
*[2]Comparative Example 2 corresponded to Example 1 of WO 2012/105431 A1. The selectively of Comparative Example 2 was replaced with the result of $^{19}$F-NMR analysis of the reaction completed solution for direct comparison with the selectivity of the present invention.
*[3]Comparative Example 3 corresponded to Example 2 of WO 2012/105431 A1. The selectively of Comparative Example 3 was replaced with the result of $^{19}$F-NMR analysis of the reaction completed solution for direct comparison with the selectivity of the present invention.

Example 14

A pressure-proof reaction vessel of stainless steel (SUS) was charged with 45 g (360 mmol, 1 eq) of α,α-difluoroacetic acid ester of the following formula, 47 mg (purity: 94.2%; 73 μmol, 0.0002 eq) of ruthenium complex of the following formula, 31 g (91 mmol as sodium methoxide, 0.25 eq) of 20% sodium ethoxide-ethanol solution and 120 mL (0.33 L/mol) of ethanol.

The inside of the reaction vessel was replaced five times with hydrogen gas. The hydrogen pressure inside the reaction vessel was set to 1.0 MPa. Then, the resulting solution inside the reaction vessel was stirred at 5° C. for 8 hours and 10 minutes. It was confirmed by $^{19}$F-NMR analysis of the reaction completed solution that: the conversion rate was 18%; and the selectivity of stable α,α-difluoroacetaldehyde equivalent of the following formula and over-reduced β,β-difluoroalcohol by-product of the following formula was 97:3.

The $^1$H- and $^{19}$F-NMR data and gas chromatographic data of the stable α,α-difluoroacetaldehyde equivalent was in agreement with those of the reference standard.

Example 15

A pressure-proof reaction vessel of stainless steel (SUS) was charged with 450 g (360 mol, 1 eq) of α,α-difluoroacetic acid ester of the following formula, 470 mg (purity: 94.2%; 730 μmol, 0.0002 eq) of ruthenium complex of the following formula, 170 g (910 mmol as sodium methoxide, 0.25 eq) of 28% sodium methoxide-methanol solution and 1.2 L (0.33 L/mol) of methanol.

The inside of the reaction vessel was replaced five times with hydrogen gas. The hydrogen pressure inside the reaction vessel was set to 1.0 MPa. Then, the resulting solution inside the reaction vessel was stirred at 15° C. for 8 hours and 10 minutes. It was confirmed by $^{19}$F-NMR analysis of the reaction completed solution that: the conversion rate was 49%; and the selectivity of stable α,α-difluoroacetaldehyde equivalent of the following formula (as a mixture of methyl and ethyl hemiacetals) and over-reduced β,β-difluoroalcohol by-product of the following formula was 95:5.

The $^1$H- and $^{19}$F-NMR data and gas chromatographic data of the stable α,α-difluoroacetaldehyde equivalent was in agreement with those of the reference standard.

Example 16

A pressure-proof reaction vessel of stainless steel (SUS) was charged with 45 g (360 mmol, 1 eq) of α,α-difluoroacetic acid ester of the following formula, 47 mg (purity: 94.2%; 73 μmol, 0.0002 eq) of ruthenium complex of the following formula, 7.0 g (36 mmol as sodium methoxide, 0.1 eq) of 28% sodium methoxide-methanol solution and 120 mL (0.33 L/mol) of methanol.

The inside of the reaction vessel was replaced five times with hydrogen gas. The hydrogen pressure inside the reaction vessel was set to 2.5 MPa. Then, the resulting solution inside the reaction vessel was stirred at 15° C. for 7 hours. It was confirmed by $^{19}$F-NMR analysis of the reaction completed solution that: the conversion rate was 87%; and the selectivity of stable α,α-difluoroacetaldehyde equivalent of the following formula (as a mixture of methyl and ethyl hemiacetals) and over-reduced β,β-difluoroalcohol by-product of the following formula was 73:27.

The $^1$H- and $^{19}$F-NMR data and gas chromatographic data of the stable α,α-difluoroacetaldehyde equivalent was in agreement with those of the reference standard.

Example 17

A pressure-proof reaction vessel of stainless steel (SUS) was charged with 45 g (360 mmol, 1 eq) of α,α-difluoroacetic acid ester of the following formula, 47 mg (purity: 94.2%; 73 μmol, 0.0002 eq) of ruthenium complex of the following formula, 3.5 g (18 mmol as sodium methoxide, 0.05 eq) of 28% sodium methoxide-methanol solution and 120 mL (0.33 L/mol) of methanol.

The inside of the reaction vessel was replaced five times with hydrogen gas. The hydrogen pressure inside the reaction vessel was set to 2.5 MPa. Then, the resulting solution inside the reaction vessel was stirred at 15° C. for 4 hours. It was confirmed by $^{19}$F-NMR analysis of the reaction completed solution that: the conversion rate was 64%; and the selectivity of stable α,α-difluoroacetaldehyde equivalent of the following formula (as a mixture of methyl and ethyl hemiacetals) and over-reduced β,β-difluoroalcohol by-product of the following formula was 82:18.

The $^1$H- and $^{19}$F-NMR data and gas chromatographic data of the stable α,α-difluoroacetaldehyde equivalent was in agreement with those of the reference standard.

Example 18

A pressure-proof reaction vessel of stainless steel (SUS) was charged with 2.2 g (20 mmol, 1 eq) of α,α-difluoroacetic acid ester of the following formula, 24 mg (50 μmol,

0.0025 eq) of ruthenium catalyst of the following formula, 350 mg (5.0 mmol, 0.25 eq) of potassium methoxide and 10 mL (0.50 L/mol) of tert-butyl methyl ether.

The inside of the reaction vessel was replaced five times with hydrogen gas. The hydrogen pressure inside the reaction vessel was set to 1.0 MPa. Then, the resulting solution inside the reaction vessel was stirred at 40° C. for 15 minutes. It was confirmed by $^{19}$F-NMR analysis of the reaction completed solution that: the conversion rate was 92%; and the selectivity of stable α,α-difluoroacetaldehyde equivalent of the following formula and over-reduced β,β-difluoroalcohol by-product of the following formula was 12:88.

The $^1$H- and $^{19}$F-NMR data and gas chromatographic data of the stable α,α-difluoroacetaldehyde equivalent was in agreement with those of the reference standards.

Figure 1:
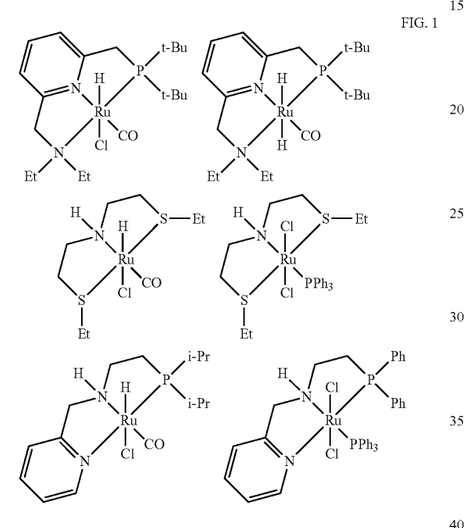

The same results were obtained even with the use of the above-mentioned existing ruthenium catalyst (described in the above-mentioned four technical documents and shown in FIG. 1) other than the ruthenium complex of the general formula [2] or [4].

Example 19

A pressure-proof reaction vessel of stainless steel (SUS) was charged with 400 g (3.6 mol, 1 eq) of α,α-difluoroacetic acid ester of the following formula, 470 mg (purity: 94.2%; 730 μmol, 0.0002 eq) of ruthenium complex of the following formula and 49 g (910 mmol, 0.25 eq) of sodium methoxide and 1.8 L (0.50 L/mol) of methanol.

The inside of the reaction vessel was replaced five times with hydrogen gas. The hydrogen pressure inside the reaction vessel was set to 1.0 MPa. Then, the resulting solution inside the reaction vessel was stirred at 15° C. for 8 hours. It was confirmed by $^{19}$F-NMR analysis of the reaction completed solution that: the conversion rate was 61%; and the selectivity of stable α,α-difluoroacetaldehyde equivalent of the following formula and over-reduced β,β-difluoroalcohol by-product of the following formula was 95:5.

The above reaction operation was repeated three times, thereby yielding the reaction completed solution equivalent to 1.2 kg (11 mol) of α,α-difluoroacetaldehyde. To the reaction completed solution, 150 g (2.5 mol, 0.23 eq) of acetic acid was added. The resulting solution was directly subjected to recovery distillation (oil bath temperature: ~66° C., vacuum degree: ~2.1 kPa) so that a methanol solution of the target product (methyl hemiacetal) was recovered. The distillation residue (i.e. solid matter containing sodium acetate and unrecovered target product) was washed by stirring with 500 mL of diisopropyl ether and filtered out. This solid matter was further washed with 500 mL of diisopropyl ether and filtered out. The thus-obtained filtrate was subjected to recovery distillation (oil bath temperature: ~66° C., vacuum degree: ~4.5 kPa) so that a diisopropyl ether solution of the target product was recovered. The recovered solutions were combined and subjected to fractional distillation (theoretical plate number: 35, distillation temperature: 92° C., vacuum degree: ~35 kPa). (At the time when the major portion of methanol and diisopropyl ether was distilled out, 850 g (19 mol, 1.7 eq) of ethanol was added to the distillation residue (containing the target product). Then, the fractional distillation was continued.) By this, 450 g of stable α,α-difluoroacetaldehyde equivalent of the following formula (as an ethyl hemiacetal) was obtained as the distillate fraction.

It was confirmed by $^1$H- and $^{19}$F-NMR analysis and gas chromatographic analysis that not only the methanol, ethanol, β,β-difluoroethanol, methyl hemiacetal and ethyl hemiacetal, but also β,β-difluoroethyl hemiacetal of the following formula and ethyl hemiacetal-derived dimer of the following formula were contained in the purified product (distillate fraction).

The purity (mol %) of the methanol, ethanol, β,β-difluoroethanol, methyl hemiacetal, ethyl hemiacetal, β,β-difluoroethyl hemiacetal and ethyl hemiacetal-derived dimer were <0.1%, 5.6%, 3.3%, 1.8%, 87.3%, 0.6% and 1.5%, respectively. The yield was approximately 30% in view of the purity. The $^1$H- and $^{19}$F-NMR data and gas chromatographic data of the ethyl hemiacetal was in agreement with those of the reference standard. The $^1$H- and $^{19}$F-NMR measurement results of the methyl hemiacetal, ethyl hemiacetal, β,β-difluoroethyl hemiacetal and ethyl hemiacetal-derived dimer are indicated below.

Methyl Hemiacetal
$^1$H-NMR (reference material: Me$_4$Si, deuterated solvent: CDCl$_3$) δ ppm; 3.53 (s, 3H), 4.62 (m, 1H), 5.60 (dt, 1H). The proton of OH group was unidentified.
$^{19}$F-NMR (reference material: C$_6$F$_6$, deuterated solvent: CDCl$_3$) δ ppm; 27.9 (ddd, 2F).

Ethyl Hemiacetal
$^1$H-NMR (reference material: Me$_4$Si, deuterated solvent: CDCl$_3$) δ ppm; 1.26 (t, 3H), 3.63 (m, 1H), 3.92 (m, 1H), 4.70 (m, 1H), 5.60 (dt, 1H). The proton of OH group was unidentified.
$^{19}$F-NMR (reference material: C$_6$F$_6$, deuterated solvent: CDCl$_3$) δ ppm; 27.9 (ddd, 2F).

[β,β-Difluoroethyl Hemiacetal]
$^1$H-NMR (reference material: Me$_4$Si, deuterated solvent: CDCl$_3$) δ ppm; 3.92 (m, 2H), 4.79 (m, 1H), 5.68 (dt, 1H), 5.91 (ddt, 1H). The proton of OH group was unidentified.
$^{19}$F-NMR (reference material: C$_6$F$_6$, deuterated solvent: CDCl$_3$) δ ppm; 27.0 (ddd, 2F), 36.1 (dt, 2F).

Ethyl Hemiacetal-Derived Dimer
$^1$H-NMR (reference material: Me$_4$Si, deuterated solvent: CDCl$_3$) δ ppm; 1.28 (t, 3H), 3.67 (m, 1H), 3.88 (m, 1H), 4.78 (m, 0.5H), 4.90 (m, 0.5H), 5.04 (m, 1H), 5.64 (m, 2H). The proton of OH group was unidentified.
$^{19}$F-NMR (reference material: C$_6$F$_6$, deuterated solvent: CDCl$_3$) δ ppm; 27.9 (m, 4F).

Example 20

A pressure-proof reaction vessel of stainless steel (SUS) was charged with 40 kg (360 mol, 1 eq) of α,α-difluoroacetic acid ester of the following formula, 47 g (purity: 94.2%; 73 mmol, 0.0002 eq) of ruthenium complex of the following formula and 18 kg (91 mol as sodium methoxide, 0.25 eq) of 28% sodium methoxide-methanol solution and 120 L (0.33 L/mol) of methanol.

The inside of the reaction vessel was replaced five times with hydrogen gas. The hydrogen pressure inside the reaction vessel was set to 0.95 MPa. Then, the resulting solution inside the reaction vessel was stirred at 6 to 11° C. for 24 hours. It was confirmed by $^{19}$F-NMR analysis of the reaction completed solution that: the conversion rate was 53%; and the selectivity of stable α,α-difluoroacetaldehyde equivalent of the following formula and over-reduced β,β-difluoroalcohol by-product of the following formula was 97:3.

Conversion rate: 53%    Selectivity: 3%
Selectivity: 97%

To the reaction completed solution, 5.3 kg (88 mol, 0.24 eq) of acetic acid was added. The resulting solution was directly subjected to recovery distillation (oil bath temperature: ~55° C., vacuum degree: ~25 kPa) so that 100 kg of a methanol solution of unreacted reaction substrate (α,α-difluoroacetic acid methyl ester) was recovered. When the methanol solution was subjected to $^{19}$F-NMR quantification by internal standard method (internal standard material: $C_6F_6$), it was confirmed that 17 kg (150 mol) of the reaction substrate was contained in the methanol solution. (In the high-boiling distillation fraction, 0.30 kg (3.7 mol) of over-reduced β,β-difluoroalcohol by-product was contained. This distillation fraction of high by-product content was disposed of as a waste.) The unreacted reaction substrate was recovered with a favorable recovery rate of approximately 90%. The recovered reaction substrate solution was recycled in the next run of hydrogenation, without problems, by adding the shortages of the reaction substrate and reaction solvent (as a matter of course, adding the predetermined amounts of ruthenium complex and base) and adjusting the content amounts of the reaction substrate and reaction solution to the predetermined levels.

The above reaction operation was repeated three times. (The unreacted reaction substrate recovered in the first and second runs was respectively recycled in the second and third runs.) After the recovery of the unreacted reaction substrate, there was obtained the distillation residue (i.e. solid matter containing sodium acetate and target product) equivalent to the result of the reaction of 1.1 kmol (1090 mol) of the α,α-difluoroacetic acid ester. The distillation residue was washed by stirring with 100 kg (2.2 kmol, 2 eq) of ethanol at 10° C. or lower and filtered out. This solid matter was further washed with a small amount of cooled ethanol and filtered out. The thus-obtained filtrate was subjected to recovery distillation (oil bath temperature: ~50° C., vacuum degree: ~0.8 kPa) so that 170 kg of an ethanol solution (1) of the target product was recovered. The distillation residue was neutralized (to pH 6 to 7) with a small amount of acetic acid. After that, the distillation residue was washed by stirring with 25 kg of ethanol, filtered out and subjected to recovery distillation in the same manner as above so that 22 kg of an ethanol solution (2) of the target product was recovered. When the ethanol solutions (1) and (2) were combined and subjected to $^{19}$F-NMR quantification by internal standard method (internal standard material: $C_6F_6$), it was confirmed that 500 mol of the target product (as a mixture of stable α,α-difluoroacetaldehyde equivalents) was contained in the combined solution. The combined solution was subjected to fractional distillation (theoretical plate number: 15, distillation temperature: ~47° C., vacuum degree: ~24 kPa). (The fractional distillation was continued, while adding ethanol as appropriate, until the selectivity of ethyl hemiacetal:methyl hemiacetal (assuming their total amount as 100) reached 95 or more:5 or less). By removal of the low-boiling distillation fraction (methanol, ethanol and β,β-difluoroethanol etc.), 70 kg of the distillation residue (purified product 1) was recovered. In this recovered product, stable α,α-difluoroacetaldehyde equivalent of the following formula was contained as a main component.

There was seen almost no loss of the target product by removal of the low-boiling distillation fraction. (So far the total yield was 46%; and the quantification value was 500 mol.) It was confirmed by $^1$H- and $^{19}$F-NMR analysis of the purified product 1 that: the purity (mol %) of the β,β-difluoroethanol, methyl hemiacetal, ethyl hemiacetal, β,β-difluoroethyl hemiacetal of the following formula and ethyl hemiacetal-derived dimer of the following formula were 4.0%, 2.7%, 86.5%, 1.8% and 4.9%, respectively; and the content amount (wt %) of the ethanol was 9.8%.

To the purified product 1, ethanol was added in an amount of 1.2 eq relative to the total amount of the β,β-difluoroethyl hemiacetal and ethyl hemiacetal-derived dimer. The resulting solution was stirred at 80° C. for 2 hours and subjected to simple distillation (distillation temperature: ~44° C., vacuum degree: ~0.5 kPa). (The low-boiling distillation fraction of high ethanol content and the distillation residue of high ethyl hemiacetal-derived dimer content were recovered and recycled.) As a result, the purified product 2 was obtained with a recovery rate of 83%. (The recovery rate was calculated based on the total amount of the stable α,α-difluoroacetaldehyde equivalents before and after the distillation.) It was confirmed by $^1$H- and $^{19}$F-NMR analysis of the purified product 2 that: the purity of the β,β-difluoroethanol, methyl hemiacetal, ethyl hemiacetal, β,β-difluoroethyl hemiacetal and ethyl hemiacetal-derived dimer were 1.9%, 2.1%, 92.2%, 0.8% and 3.0%, respectively; and the content amount of the ethanol was 6.5%. It was possible by this operation to reduce the content amounts of the methyl hemiacetal, β,β-difluoroethyl hemiacetal and ethyl hemiacetal-derived dimer and increase the content amount of the ethyl hemiacetal.

Differently from the above process, there was a case where the content amount of the ethyl hemiacetal-derived dimer was significantly increased when the low-boiling distillation fraction was removed until the coexistence amount of the ethanol reached a relatively small level (in particular, 3 wt % or less). For example, the purity of the β,β-difluoroethanol, methyl hemiacetal, ethyl hemiacetal, β,β-difluoroethyl hemiacetal and ethyl hemiacetal-derived dimer became 2.7%, 1.6%, 78.8%, 3.3% and 13.6%, respectively. (The content amount of the ethanol became 2.3%.) Even in such a case, it was possible by the above purification operation to purify the β,β-difluoroethanol, methyl hemiacetal, ethyl hemiacetal, β,β-difluoroethyl hemiacetal and ethyl hemiacetal-derived dimer to 1.9%, 1.2%, 91.7%, 0.9% and 4.3%, respectively. (The content amount of the ethanol was increased to 6.4%).

Example 21

A pressure-proof reaction vessel of stainless steel (SUS) was charged with 45 kg (360 mol, 1 eq) of α,α-difluoroacetic acid ester of the following formula, 47 g (purity: 94.2%; 73 mmol, 0.0002 eq) of ruthenium complex of the following formula and 18 kg (91 mol as sodium methoxide, 0.25 eq) of 28% sodium methoxide-methanol solution and 120 L (0.33 L/mol) of methanol.

The inside of the reaction vessel was replaced five times with hydrogen gas. The hydrogen pressure inside the reaction vessel was set to 1.0 MPa. Then, the resulting solution inside the reaction vessel was stirred at 30° C. for 15 minutes and at 20° C. for 6 hours. It was confirmed by $^{19}$F-NMR analysis of the reaction completed solution that: the conversion rate was 52%; and the selectivity of stable α,α-difluoroacetaldehyde equivalent of the following formula (as a mixture of methyl and ethyl hemiacetals) and over-reduced β,β-difluoroalcohol by-product of the following formula was 95:5.

To the reaction completed solution, 5.3 kg (88 mol, 0.24 eq) of acetic acid was added. The resulting solution was directly subjected to recovery distillation (distillation temperature: ~44° C., vacuum degree: ~31 kPa) so that 100 kg of a methanol solution of unreacted reaction substrate (as a mixture of α,α-difluoroacetic acid methyl ester as a major component and α,α-difluoroacetic acid ethyl ester) was recovered. When the methanol solution was subjected to $^{19}$F-NMR quantification by internal standard method (internal standard material: $C_6F_6$), it was confirmed that 160 mol of the reaction substrate (as the total amount of the methyl and ethyl esters) was contained in the methanol solution. (In the high-boiling distillation fraction, 3.8 mol of over-reduced β,β-difluoroalcohol by-product, 200 mol of ethanol and 5.9 mol of stable α,α-difluoroacetaldehyde equivalents (as a mixture of methyl and ethyl hemiacetals) were contained. This distillation fraction of high by-product content was disposed of as a waste.) The unreacted reaction substrate was recovered with a favorable recovery rate of 92%. The recovered reaction substrate solution was recycled in the next run of hydrogenation, without problems, by adding the shortages of the reaction substrate and reaction solvent (as a matter of course, adding the predetermined amounts of ruthenium complex and base) and adjusting the content amounts of the reaction substrate and reaction solution to the predetermined levels.

The above reaction operation was repeated three times. (The unreacted reaction substrate recovered in the first and second runs was respectively recycled in the second and third runs.) There was thus obtained the distillation residue (i.e. solid matter containing sodium acetate and target product) equivalent to the result of the reaction of 1.1 kmol (1088 mol) of the α,α-difluoroacetic acid ester. The distillation residue was treated by the same operation as in Example 20. Then, 70 kg of the distillation residue (purified product 1) was recovered. In this recovered product, stable α,α-difluoroacetaldehyde equivalent of the following formula was contained as a main component.

So far the total yield was 46%; and the total quantification value of stable α,α-difluoroacetaldehyde equivalents was 500 mol. It was confirmed by $^1$H- and $^{19}$F-NMR analysis of the purified product 1 that: the purity (mol %) of the β,β-difluoroethanol, methyl hemiacetal, ethyl hemiacetal, β,β-difluoroethyl hemiacetal of the following formula and ethyl hemiacetal-derived dimer of the following formula were 1.3%, 4.0%, 83.4%, 1.2% and 10.1%, respectively; and the content amount (wt %) of the ethanol was 4.5%.

The purified product 1 was treated by the same operation as in Example 20. As a result, the purified product 2 was obtained with a recovery rate of 80%. It was confirmed by

¹H- and ¹⁹F-NMR analysis of the purified product 2 that: the purity of the β,β-difluoroethanol, methyl hemiacetal, ethyl hemiacetal, β,β-difluoroethyl hemiacetal and ethyl hemiacetal-derived dimer were 0.6%, 1.5%, 91.8%, 0.4% and 5.7%, respectively; and the content amount of the ethanol was 6.5%.

Example 22

Provided was a diisopropyl ether solution of stable α,α-difluoroacetaldehyde equivalent of the following formula (as a methyl hemiacetal).

The solution was subjected to decomposition by heating (oil bath temperature: ~133° C.), thereby generating a gas of α,α-difluoroacetaldehyde of the following formula.

The diisopropyl ether fraction was recovered. The ¹H- and ¹⁹F-NMR measurement results of the α,α-difluoroacetaldehyde are indicated below. The above structure was confirmed by mass analysis of the generated gas. It was also confirmed that a self-polymerization product of the α,α-difluoroacetaldehyde was increased with the progress of time.

¹H-NMR (reference material: Me₄Si, deuterated solvent: CDCl₃) δ ppm; 5.73 (t, 1H), 9.54 (s, 1H).
¹⁹F-NMR (reference material: C₆F₆, deuterated solvent: CDCl₃) δ ppm; 30.9 (d, 2F).

Example 23

Diphosphorus pentoxide was added to stable α,α-difluoroacetaldehyde equivalent of the following formula (as an ethyl hemiacetal).

The resulting mixture was heated (oil bath temperature: ~110° C.), thereby generating a gas of α,α-difluoroacetaldehyde of the following formula.

The generated gas was bubbled into cooled methanol. By this, a methanol solution of stable α,α-difluoroacetaldehyde equivalent of the following formula (as a methyl hemiacetal) was recovered. The recovery rate was approximately 80%.

INDUSTRIAL APPLICABILITY

The α,α-difluoroacetaldehyde produced by the present invention is usable as intermediates for pharmaceutical and agrichemical products.

The invention claimed is:
1. A method for producing α,α-difluoroacetaldehyde of the formula [3], comprising: reaction of an α,α-difluoroacetic acid ester of the general formula [1] with hydrogen gas ($H_2$) in the presence of a homogeneous ruthenium catalyst and a base,

[1]

where $R^1$ represents an alkyl group or a substituted alkyl group,

[3]

2. The method according to claim 1, wherein the α,α-difluoroacetic acid ester of the general formula [1] is an α,α-difluoroacetic acid ester of the general formula [5],

[5]

where $R^2$ is an alkyl group.
3. The method according to claim 1, wherein the reaction is performed at a reaction temperature of 30° C. or lower with the use of an alcohol solvent as a reaction solvent.
4. The method according to claim 3, wherein the reaction is performed at a reaction temperature of 20° C. or lower with the use of an alcohol solvent as a reaction solvent.
5. The method according to claim 1, wherein the reaction is performed at a reaction temperature of 50° C. or lower with the use of an aliphatic hydrocarbon solvent, an aromatic hydrocarbon solvent, a halogenated solvent, or an ether solvent as a reaction solvent.
6. The method according to claim 5, wherein the reaction is performed at a reaction temperature of 40° C. or lower with the use of an aliphatic hydrocarbon solvent, an aromatic hydrocarbon solvent, a halogenated solvent, or an ether solvent as a reaction solvent.
7. The method according to claim 1, further comprising: stopping the reaction at the time when the selectivity of the α,α-difluoroacetaldehyde of the formula [3] and β,β-difluoroethanol is α,α-difluoroacetaldehyde:β,β-difluoroethanol=90 or more:10 or less; and recovering and recycling unreacted α,α-difluoroacetic acid ester.

8. The method according to claim 1, further comprising post-treatment to, when the α,α-difluoroacetaldehyde is obtained as a stable equivalent of the general formula [6] or [7], purify the α,α-difluoroacetaldehyde as a hemiacetal of the general formula [8] by contact of the stable equivalent with methanol or ethanol,

[6]

where R³ represents a methyl group or an ethyl group,

[7]

where R⁴ represents a methyl group or an ethyl group,

[8]

9. A method for producing α,α-difluoroacetaldehyde of the formula [3], comprising: reaction of an α,α-difluoroacetic acid ester of the general formula [1] with hydrogen gas (H₂) in the presence of a ruthenium catalyst,

[1]

where R¹ represents an alkyl group or a substituted alkyl group,

[3]

wherein the ruthenium catalyst is any of those represented by the following formulas.

-continued

10. The method according to claim 9, wherein the reaction is performed in the presence of a base.

11. The method according to claim 9, wherein the reaction is performed at a reaction temperature of 30° C. or lower with the use of an alcohol solvent as a reaction solvent.

12. The method according to claim 11, wherein the reaction is performed at a reaction temperature of 20° C. or lower with the use of an alcohol solvent as a reaction solvent.

13. The method according to claim 9, wherein the reaction is performed at a reaction temperature of 50° C. or lower with the use of an aliphatic hydrocarbon solvent, an aromatic hydrocarbon solvent, a halogenated solvent, or an ether solvent as a reaction solvent.

14. The method according to claim 13, wherein the reaction is performed at a reaction temperature of 40° C. or lower with the use of an aliphatic hydrocarbon solvent, an aromatic hydrocarbon solvent, a halogenated solvent, or an ether solvent as a reaction solvent.

15. The method according to claim 9, further comprising:
stopping the reaction at the time when the selectivity of the α,α-difluoroacetaldehyde of the formula [3] and β,β-difluoroethanol is α,α-difluoroacetaldehyde:β,β-difluoroethanol=90 or more:10 or less; and
recovering and recycling unreacted α,α-difluoroacetic acid ester.

16. The method according to claim 9, further comprising post-treatment to, when the α,α-difluoroacetaldehyde is obtained as a stable equivalent of the general formula [6] or [7], purify the α,α-difluoroacetaldehyde as a hemiacetal of the general formula [8] by contact of the stable equivalent with methanol or ethanol,

[6]

where R³ represents a methyl group or an ethyl group,

[7]

where R⁴ represents a methyl group or an ethyl group,

[8]

* * * * *